United States Patent [19]
Boyd et al.

[11] Patent Number: 5,227,138
[45] Date of Patent: Jul. 13, 1993

[54] BLOOD TRANSPORT APPARATUS

[75] Inventors: Karen A. Boyd, Seattle; Dana Fayette, Sultan, both of Wash.

[73] Assignee: Virginia Mason Clinic, Seattle, Wash.

[21] Appl. No.: 942,520

[22] Filed: Sep. 9, 1992

[51] Int. Cl.$^5$ .................. G01N 33/16; B01F 13/08
[52] U.S. Cl. .................. 422/102; 73/864.91; 211/71; 422/99; 422/100; 366/273; 366/274
[58] Field of Search .......... 422/102, 99, 100; 73/864.91, 864.01; 248/206.5, 232; 211/71, 79, 74, 84, 89, 94; 366/273, 274, 341, 346; 128/760, 763, 768–770; 220/352, 353

[56] References Cited

U.S. PATENT DOCUMENTS

| | | | |
|---|---|---|---|
| 2,459,224 | 1/1949 | Hendricks | 259/108 |
| 3,010,569 | 11/1961 | Goldman | 220/352 |
| 3,175,553 | 3/1965 | Mattson | 128/2 |
| 3,219,318 | 11/1965 | Hershler | 422/257 |
| 3,388,043 | 6/1968 | Ingvorsen | 195/139 |
| 3,888,466 | 6/1975 | Sedam | 259/44 |
| 3,983,996 | 10/1976 | Hendren, III | 206/363 |
| 3,985,649 | 10/1976 | Eddelman | 436/177 |
| 3,997,272 | 12/1976 | George | 356/246 |
| 4,045,185 | 8/1977 | Azemar et al. | 259/102 |
| 4,111,302 | 9/1978 | Roth | 206/363 |
| 4,200,613 | 4/1980 | Alfrey et al. | 422/71 |
| 4,214,874 | 7/1980 | White | 422/100 |
| 4,264,559 | 4/1981 | Price | 422/104 |
| 4,355,906 | 10/1982 | Ono | 366/274 |
| 4,441,510 | 4/1984 | Worley et al. | 128/763 |
| 4,585,623 | 4/1986 | Chandler | 422/102 |
| 4,653,511 | 3/1987 | Goch | 128/763 |
| 4,728,500 | 3/1988 | Higo | 422/99 |
| 4,944,924 | 7/1990 | Mawhirt et al. | 211/71 |
| 4,976,271 | 12/1990 | Blair | 128/763 |

Primary Examiner—Jill A. Johnston
Assistant Examiner—Ramon Torres
Attorney, Agent, or Firm—Seed and Berry

[57] ABSTRACT

An apparatus for transporting blood samples within a capillary tube using a rigid plate member to protect the capillary tube during transport. A magnet is magnetically coupled with and thereby moves a ferrous metal flea within the capillary tube to promote mixing of the blood sample and an anticoagulant chemical coating on the inside of the capillary tube. The magnet is slid along the length of a recessed guide track or guide members to assure that the magnet does not come in contact with the capillary tube with sufficient force to break the capillary tube. The magnet has a central archway through which the capillary tube extends to increase the magnetic coupling between the magnet and the flea and yet prevent contact with the capillary tube. The capillary tube is held within an alignment groove in the rigid plate member. In one embodiment, a holder holds the capillary tube against the rigid plate. A recess is provided to receive one end of the capillary tube and a slot is provided to receive the other end of the capillary tube to help retain the tube. An opening through the rigid plate member near the slot allows the easy extraction of the capillary tube from the apparatus.

17 Claims, 3 Drawing Sheets

BLOOD TRANSPORT APPARATUS

TECHNICAL FIELD

The present invention relates to an apparatus for transporting blood samples. More specifically, the present invention relates to an apparatus for transporting a capillary tube containing a micro blood sample.

BACKGROUND OF THE INVENTION

During the course of labor and delivery or other medical procedures, it is often necessary to obtain a micro blood sample at the site where the patient is located and then transport the blood sample to the laboratory for analysis. In certain situations, such as fetal blood testing, only a small amount of blood may be available for testing. The blood sample is generally drawn into a small diameter glass capillary tube. The internal surface of the capillary tube is coated with heparin or another suitable chemical anticoagulant to maintain the blood in a liquid form for testing. To promote mixing of the blood with the chemical anticoagulant, a small metal cylinder known as a "flea" is placed inside the capillary tube. The flea is made of ferrous metal which causes the flea to be attracted to a magnet. The diameter of the flea is smaller than the inside diameter of the capillary tube, thus allowing the flea to move freely inside the capillary tube through the blood sample therein. A ring magnet with the capillary tube extending therethrough is moved up and down the length of the capillary tube, causing the flea inside the capillary tube to also move up an down the capillary tube, thereby stirring the blood sample and mixing it with the chemical anticoagulant.

When a blood sample is withdrawn, the ends of the capillary tube are sealed for transportation using conventional test tube sealing putty or rubber boot caps. A lab technician or other medical personnel must then quickly hand carry the capillary tube with the blood sample from the blood withdrawal site to the laboratory so that the blood sample may be analyzed and a report returned to the attending physician. This is especially important in child labor and delivery, where the results of the blood test may dictate whether a Caesarian section must be performed. Under a time-critical circumstance such as this, the blood sample must be quickly transported to the laboratory, while keeping the fragile capillary tube intact and using the ring magnet and the flea to prevent coagulation of the blood sample. If the capillary tube should break or the blood coagulate, the sample may not be suitable to assure test results. In a labor and delivery situation, there may not be time to extract another blood sample for testing. Typically, the capillary tube containing the blood sample is transported by a technician holding the fragile capillary tube in one hand while grasping and reciprocally moving the ring magnet along the length of the capillary tube using the other hand. These twin tasks must often be accomplished while quickly walking through a crowded hospital hallway or taking a crowded elevator between the blood withdrawal site and the laboratory.

The fragility of the capillary tube and the need to constantly slide the magnet up and down the tube makes it difficult to quickly transport the capillary tube without breaking it. Therefore, it can be appreciated that there is a significant need for an apparatus to safely transport blood samples while allowing a magnet to slide freely about the capillary tube without breaking it. The present invention fulfills these needs, and further provides other related advantages.

SUMMARY OF THE INVENTION

The present invention resides in an apparatus for transporting a blood sample in a capillary tube containing a ferrous metal flea for mixing the blood sample with a chemical anticoagulant within the capillary tube. The apparatus includes an elongated rigid support member having longitudinally spaced apart first and second end portions, and a magnet movable longitudinally along the support member between the first and second support member end portions. The capillary tube is positioned adjacent to the magnet, and longitudinal movement of the magnet causes a corresponding movement of the metal flea inside the capillary tube.

The apparatus further includes a magnet guide extending longitudinally along the support member to guide the magnet for longitudinal reciprocating movement between the first and second support member end portions. In the illustrated embodiments, the support member has an alignment groove formed therein with a size to receive the capillary tube. The alignment groove extends longitudinally generally between the first and second support member end portions. The magnet has a central archway through which the capillary tube extends when the magnet is moved between the first and second support member end portions. An opening is provided within the support member to provide access to the capillary tube to aid in the removal of the capillary tube from the apparatus.

In one embodiment, the guide is a recessed track. The track is formed by first and second sidewalls extending longitudinally between the first and second support member end portions, and by first and second endwalls at the first and second support member end portions. The track further has a recessed surface extending at least partially between the first and second guide track endwalls and providing a surface over which the magnet slides. An aperture is formed in the first guide track endwall and has a size to receive and restrain movement of one end of the capillary tube therein. Also, a slot is provided within the second guide track endwall sized to receive and restrain lateral movement of the other end of the capillary tube therein. The slot extends in a direction away from the recessed surface.

In another illustrated embodiment, the guide includes at least one guide member with the magnet slideably mounted thereon.

Other features and advantages of the apparatus will become apparent from the following detailed description, taken in conjunction with the accompanying drawings.

DETAILED DESCRIPTION OF THE INVENTION

Figure 1:
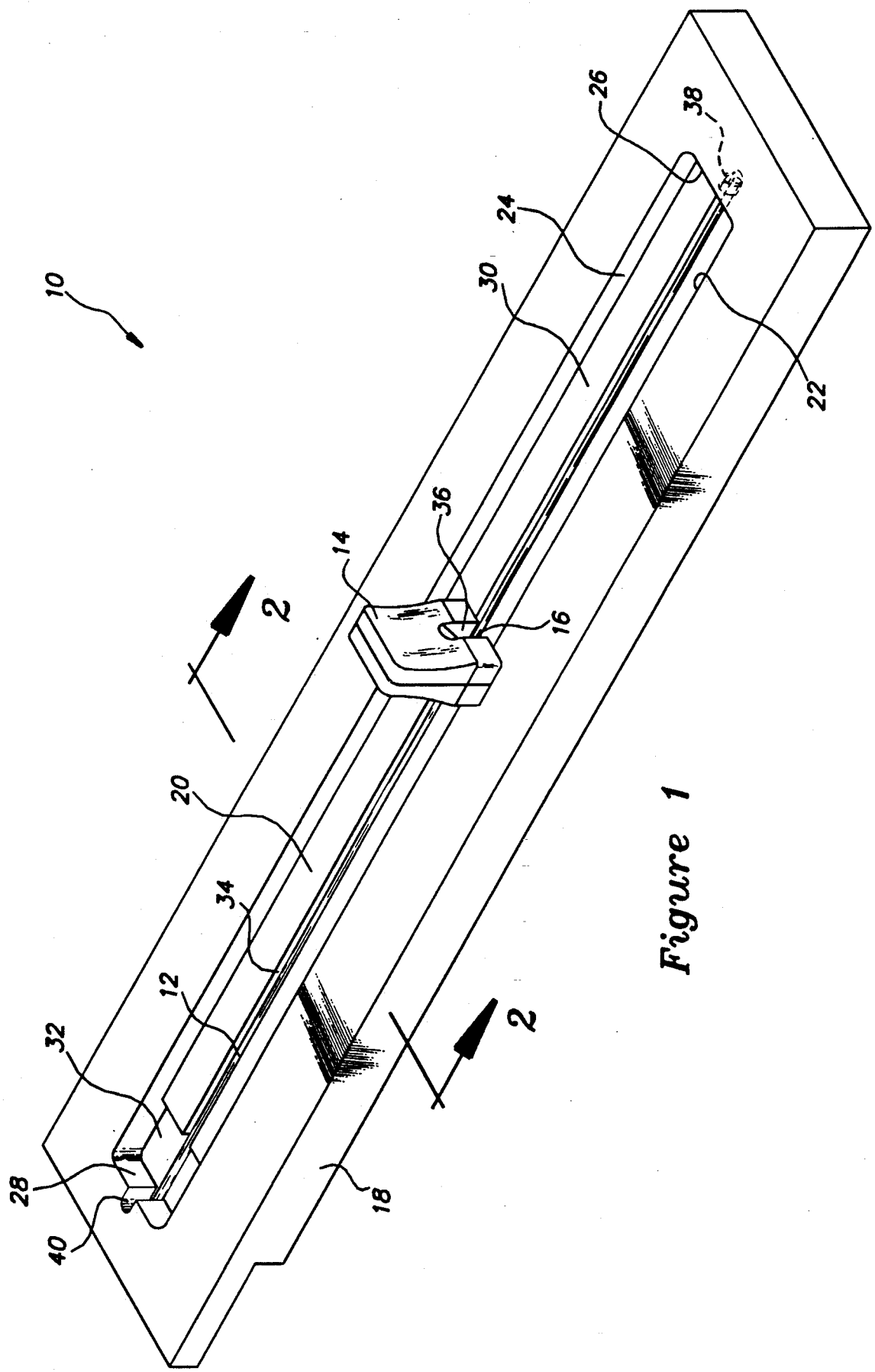
FIG. 1 is an isometric view of a blood transport apparatus embodying the present invention.

The present invention resides in an apparatus, indicated generally by the reference numeral 10, which holds a fragile glass capillary tube 12 stationary in a protected position while allowing a magnet 14 to freely move along the capillary tube, thus causing a flea 16 therein to move within the capillary tube. As shown in FIG. 1, the apparatus 10 includes an elongated rigid plate member 18 containing a longitudinally extending guide track 20. The guide track 20 has a pair of elongated parallel opposing sidewalls 22 and 24, and a pair of parallel opposing endwalls 26 and 28. The guide track 20 is fully open on its top side and has a bottom wall 30 which extends laterally fully between the sidewalls 22 and 24. The bottom wall 30 extends longitudinally from the endwall 26 to a position spaced from the endwall 28, thus defining an opening 32 in the bottom wall.

Figure 2:
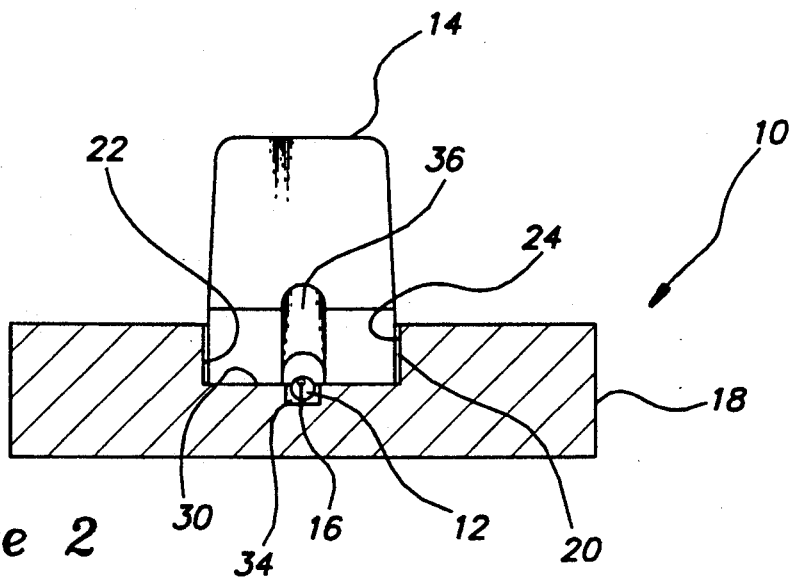
FIG. 2 is a cross-sectional view taken substantially along line 2—2 of FIG. 1.

The width of the guide track 20 between the sidewalls 22 and 24 is sized to allow the magnet 14 to slide longitudinally freely within the guide track 20 resting on the bottom wall 30 in response to the force applied thereto by the hand of the person using the apparatus 10, while at the same time preventing the magnet from twisting sideways and breaking the capillary tube 12 which is centrally positioned within the guide track 20 in a longitudinally extending alignment groove 34. As best seen in FIG. 2, the capillary tube 12 is positioned in the alignment groove 34 at least partially below the level of the guide track bottom wall 30.

To avoid contact with the portion of the capillary tube 12 projecting above the level of the guide track bottom wall 30, the magnet 14 has at a lower end a central archway 36 through which the capillary tube 12 extends. The central archway 36 allows the magnet 14 to be closer to the flea 16 within the capillary tube 12 and hence results in a greater magnetic coupling between the magnet and the flea. The magnetic coupling between the magnet 14 and the flea 16 causes the flea to move within the capillary tube 12 as the magnet is slid back and forth along the length of the guide track 20 by the user of the apparatus 10. The user of the apparatus 10 is generally a lab technician who must carry the blood sample to the laboratory. The rigid plate member 18 gives the user something that can be firmly and securely grasped in one hand while the other hand is used to slide the magnet 14 back and forth in the guide track 20. This motion causes a corresponding reciprocating movement in the flea 16 within the capillary tube 12, thus causing the blood sample to mix with a chemical anticoagulant coating on the inside of the capillary tube.

A recess 38 in the endwall 26 at one end of the guide track 20 is aligned with the alignment groove 34 and is sized to receive and retain therein one end of the capillary tube 12. At the opposite end of the guide track 20, a vertically extending slot 40 in the endwall 28, also aligned with the alignment groove 34, is provided to receive and restrain against lateral movement the other end of the capillary tube 12. The recess 30 and the slot 40 help to hold the capillary tube 12 in alignment within the guide track 20, as does the alignment groove 34, so it is positioned within the central archway 36 of the magnet 14, but also helps retain the capillary tube in place in the apparatus 10 during transport.

Figure 3:
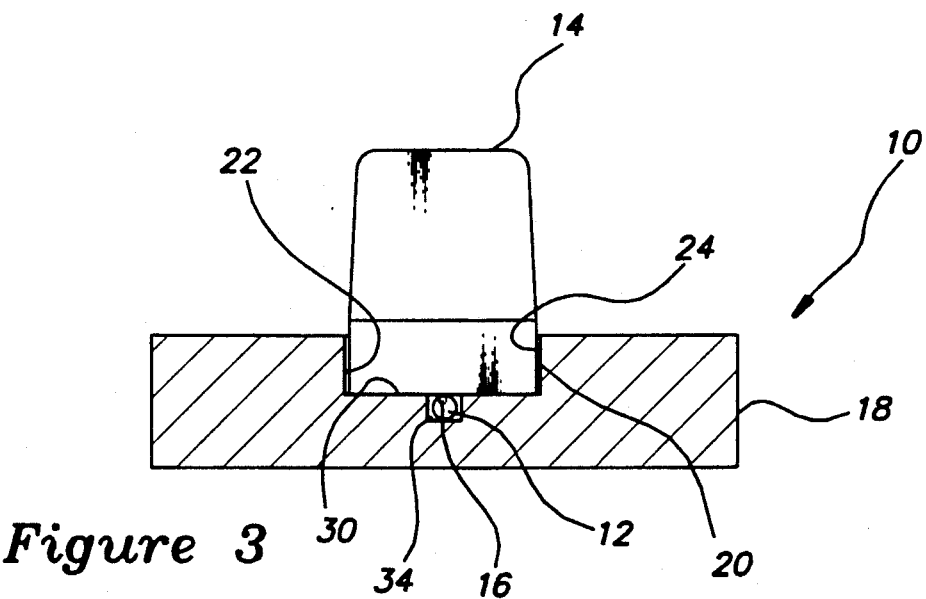
FIG. 3 is a cross-sectional view of a first alternative embodiment of the present invention.
Figure 5:
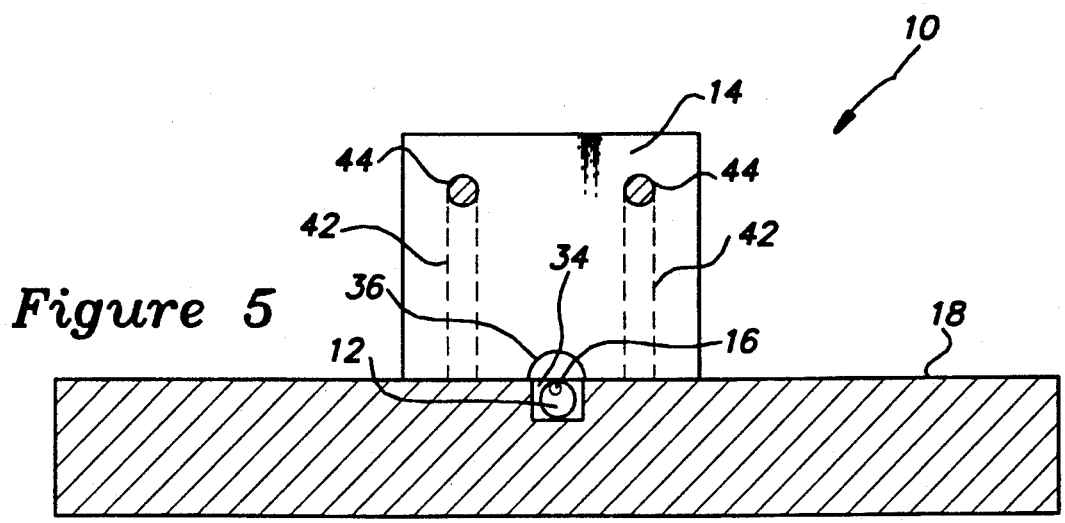
FIG. 5 is a cross-sectional view taken substantially along line 5—5 of FIG. 4.

The alignment groove 34 may simply be a shallow groove allowing the capillary tube to rest partially within the alignment groove, or may be large enough to accommodate the entire capillary tube as shown in the alternative embodiment of FIG. 3. In the embodiment of FIG. 3 the central archway of the magnet 14 has been eliminated.

The opening 32 in the bottom wall 30 extends fully through the rigid plate member 18 at a position adjacent to the slot 40 and is used to help remove the capillary tube 12 from the guide track 20 and the alignment groove 34. The opening 32 may be conveniently sized to accommodate a finger of the user so that the user may press on the capillary tube 12 from below to push the end of the capillary tube in the slot 40 free thereof so the end may be grasped and the other end of the capillary tube pulled out of the recess 26 and completely free of the apparatus 10.

In this manner, the capillary tube 12 may be quickly and easily transported from the blood withdrawal site to the laboratory, while minimizing the danger of breaking the capillary tube during transport. However, the apparatus 10 also allows the user to slide the magnet 14 back and forth over the capillary tube 12 as it is carried to the laboratory. The guide track 20 restrains lateral and twisting movement of the magnet 14 to prevent the magnet from contacting the capillary tube 12 with a great enough force to cause breakage of the capillary tube.

Figure 4:
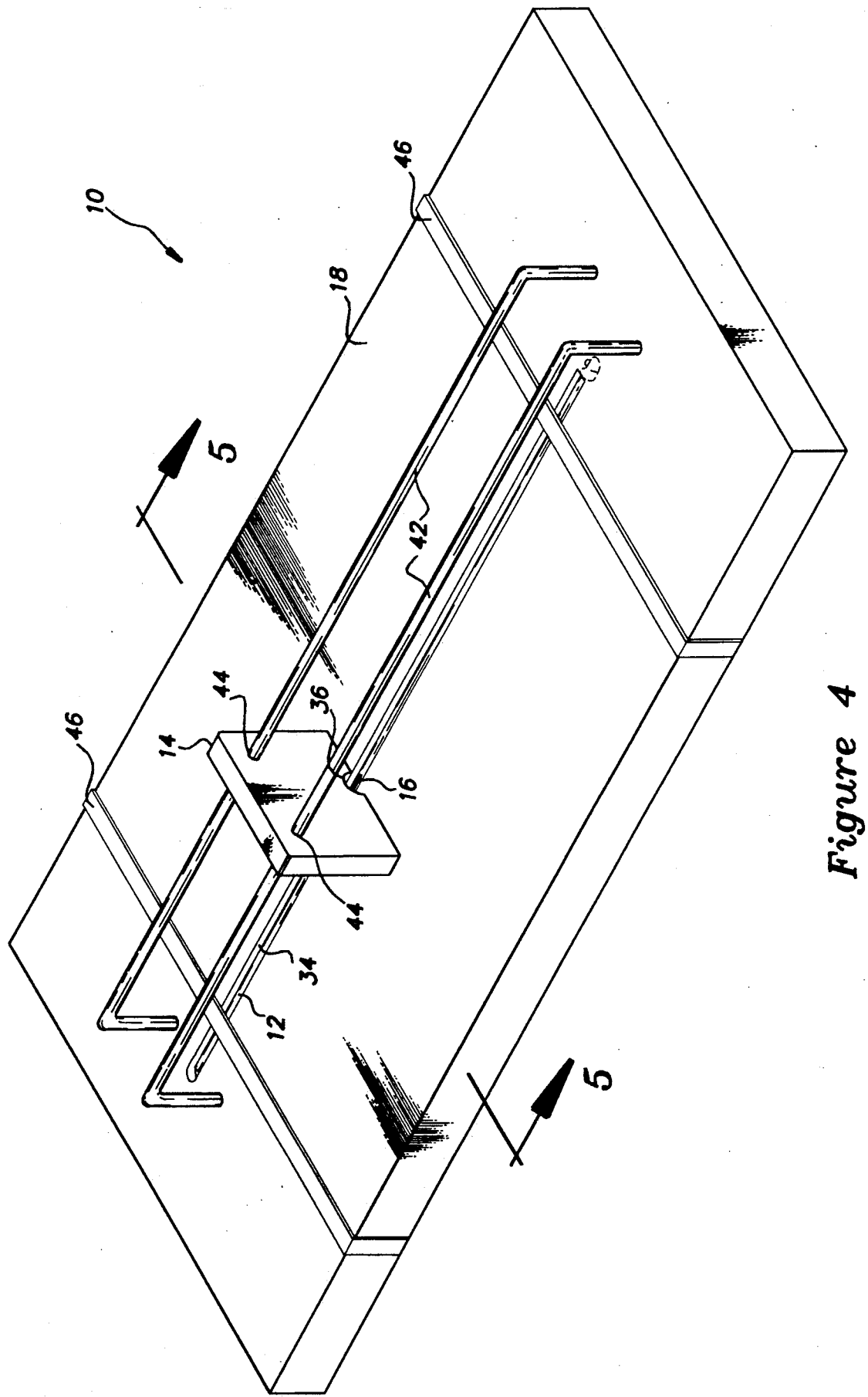
FIG. 4 is an isometric view of a second alternative embodiment of the present invention.

In an alternative embodiment of the apparatus 10 shown in FIG. 4, the magnet 14 is guided by a pair of stand-off guide rods 42, which extend through corresponding holes 44 in the magnet. The guide rods 42 may be made of plastic or any other suitable non-magnetic material. The magnet holes 44 allow the magnet 14 to slide freely along the guide rods 42 while maintaining the position of the magnet with respect to the capillary tube 12. The guide track 20 has been eliminated in this embodiment. One or more holding members 46 are used to hold the capillary tube 12 securely within the alignment groove 34. The holding members 46 may be as simple as the illustrated rubber bands, or may comprise sliding latches, hinges, or the like. Although not illustrated, a recess, slot and opening may be used in this embodiment as used in the embodiment of FIG. 1 to help maintain the position of the capillary tube 12 within the alignment groove 34 and provide for its easy removal.

It is to be understood that, even though numerous embodiments and advantages of the present invention have been set forth in the foregoing description, the above disclosure is illustrative only and changes may be made in detail yet remain within the broad principles of the invention. Therefore, the present invention is to be limited only by the appended claims.

We claim:

1. An apparatus for transporting a blood sample in a capillary tube containing a ferrous metal flea for mixing the blood sample with a chemical anticoagulant within the capillary tube, the apparatus comprising:

an elongated rigid support member having longitudinally spaced apart first and second end portions;

a magnet guide track extending longitudinally along said support member, said guide track being recessed into said support member and having first and second guide track sidewalls extending longitudinally between said first and second support member end portions, said guide track further having first and second guide track endwalls at said first and second support member end portions, respectively, and a recessed surface, said recessed surface extending at least partially between said first and second guide track endwalls and being laterally bounded by said first and second guide track sidewalls, means for positioning a capillary tube within said guide track and extending longitudinally between said first and second guide track endwalls, said positioning means including an aperture and a slot;

a magnet positionable within said guide track and slideable longitudinally along said recessed surface, with the capillary tube in position adjacent thereto, the longitudinal movement of said magnet within said guide track causing a corresponding movement of a metal flea inside the capillary tube, said magnet having a width extending substantially fully between said first and second guide track sidewalls so as to restrict lateral movement of said magnet within said guide track;

said aperture being within said first guide track endwall sized to receive therein and restrict movement of one end of the capillary tube; and said slot being within said second guide track endwall sized to receive therein and restrict lateral movement of the other end of the capillary tube, said slot extending in a direction away from said recessed surface, whereby the capillary tube can be safely transported within said recessed guide track as the magnet is slid back and forth therein to mix the blood sample and a chemical anticoagulant, and easily removed from the recessed guide track when desired.

2. The apparatus of claim 1 wherein said magnet has a central archway through which the capillary tube extends when said magnet is moved longitudinally along said guide track, whereby a magnetic coupling is provided between said magnet and the metal flea.

3. The apparatus of claim 1 wherein said positioning means further includes an alignment groove in said recessed surface, said alignment groove extending between said aperture and said slot and sized to receive the capillary tube therein.

4. The apparatus of claim 2, further including an opening within said support member adjacent to said second guide track endwall to aid in the removal of the end of the capillary tube from said slot.

5. An apparatus for transporting a blood sample in a capillary tube containing a ferrous metal flea for mixing the blood sample with a chemical anticoagulant within the capillary tube, the apparatus comprising:

an elongated rigid support member having longitudinally spaced apart first and second end portions;

a recessed guide track extending longitudinally within said support member between first and second guide track endwalls at said first and second support member end portions, respectively, and having a recessed surface, said recessed surface extending at least partially between said first and second guide track endwalls, means for positioning a capillary tube within said recessed guide track and extending longitudinally between said first and second guide track endwalls; and a magnet positionable within said recessed guide track and slideable longitudinally along said recessed surface, with the capillary tube in position adjacent thereto, the longitudinal movement of said magnet within said recessed guide track causing a corresponding movement of a metal flea inside the capillary tube.

6. The apparatus of claim 5 wherein said magnet has a central archway through which the capillary tube extends when said magnet is slid along said recessed guide track, whereby a magnetic coupling is provided between said magnet and the metal flea.

7. The apparatus of claim 5 wherein said positioning means includes a longitudinally extending alignment groove in said recessed surface sized to receive the capillary tube therein.

8. The apparatus of claim 5, further including an access opening in said recessed surface to aid in the removal of the capillary tube from the apparatus.

9. The apparatus of claim 5, further including a first receiver located toward one end of said recessed guide track and sized to receive therein and restrict movement of one end of the capillary tube; and a second receiver located toward an opposite end of said recessed guide track and sized to receive therein and restrict movement of the other end of the capillary tube.

10. An apparatus for transporting a blood sample in a capillary tube containing a ferrous metal flea for mixing the blood sample with a chemical anticoagulant within the capillary tube, the apparatus comprising:

an elongated rigid support member having longitudinally spaced apart first and second end portions;

an alignment groove in said support member sized to receive a capillary tube therein;

a magnet movable longitudinally along said support member between said first and second support member end portions, with the capillary tube in position adjacent thereto, the longitudinal movement of said magnet causing a corresponding movement of a metal flea inside the capillary tube; and a magnet guide extending longitudinally along said support member, said magnet guide guiding said magnet for longitudinal reciprocating movement between said first and second support member end portions, and restricting lateral movement of said magnet along said support member.

11. The apparatus of claim 10 wherein said magnet has a central archway through which the capillary tube extends when said magnet is moved between said first and second support member end portions.

12. The apparatus of claim 10, further including an opening within said support member to provide access to the capillary tube to aid in the removal of the capillary tube from the apparatus.

13. The apparatus of claim 10 wherein said magnet guide is a recessed track.

14. The apparatus of claim 10 wherein said magnet guide includes at least one guide member with said magnet slideably mounted thereon.

15. An apparatus for transporting a blood sample in a capillary tube containing a ferrous metal flea for mixing the blood sample with a chemical anticoagulant within the capillary tube, the apparatus comprising:

an elongated rigid support member having longitudinally spaced apart first and second end portions, said support member being sized to support a capillary tube with the capillary tube extending longitudinally between said first and second support member end portions;

a magnet movable longitudinally along said support member between said first and second support member end portions, with the capillary tube in position adjacent thereto, the longitudinal movement of said magnet causing a corresponding movement of a metal flea inside the capillary tube; and a magnet guide extending longitudinally along said support member, said magnet guide guiding said magnet for longitudinal reciprocating movement between said first and second support member end portions.

16. The apparatus of claim 15 wherein said magnet has a central archway through which the capillary tube extends when said magnet is moved between said first and second support member end portions.

17. The apparatus of claim 15, further including an opening within said support member to provide access to the capillary tube to aid in the removal of the capillary tube from the apparatus.

* * * * *